United States Patent
Reinhard et al.

(10) Patent No.: US 6,809,194 B1
(45) Date of Patent: Oct. 26, 2004

(54) AKT3 INHIBITORS

(75) Inventors: Christoph Reinhard, Alameda, CA (US); Anne B. Jefferson, Oakland, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/851,670

(22) Filed: May 8, 2001

Related U.S. Application Data

(60) Provisional application No. 60/203,543, filed on May 10, 2000.

(51) Int. Cl.$^7$ .......................... C07H 21/04; C12Q 1/68; C12N 15/85; C12N 15/86; C12P 19/34
(52) U.S. Cl. .................. 536/24.5; 536/24.3; 536/24.31; 536/24.33; 435/6; 435/91.1; 435/325; 435/366; 435/375
(58) Field of Search ........................... 435/6, 91.1, 325, 435/366, 375; 514/44; 536/23.1, 24.5, 24.31, 24.3, 24.33

(56) References Cited

U.S. PATENT DOCUMENTS

| | | |
|---|---|---|
| 5,958,773 A | 9/1999 | Monia et al. |
| 6,187,586 B1 * | 2/2001 | Monia et al. |

OTHER PUBLICATIONS

Jen et al., Stem Cells, vol. 18, pp. 307–319, 2000.*
Green et al. J. of Am. Coll. Surg. vol. 191, No. 1, Jul. 2000.*
Agrawal et al. Molecular Medicine Today, vol. 6, pp; 72–81, Feb. 2000.*
Ma et al., Biotechnology Annula Review, vol. 5, pp. 155–196, 2000.*
Branch, TIBS 23, pp. 45–50, Feb. 1998.*
Flanagan et al., Nature Biotechnology, vol. 17, No. 1, pp. 48–52, Jan. 1999.*
Bennett et al. "Pharmacology of Antisense Therapeutic Agents", Chapter 2, from Methods in Molecular Medicine: Antisense Therapeutics, Ed. S. Agrawal, Humana Press Inc., Totowa, NJ, ISBN: 0_89603-305-8, 1996.*
Masure et al., Eur. J. Biochem., vol. 265, pp. 353–360, 1999.*
Konishi et al. Biochemical and Biophysical Research Communications, vol. 216, No. 2, Nov. 13, 1995, pp. 526–534.*
Nakatani et al., Biochemical and Biophysical Research Communications, vol. 257, pp. 906–910, 1999.*
Brodbeck et al., The Journal of Biological Chemistry, vol. 274, No. 14, pp. 9133–9136, 1999.*
Alessi et al., "Mechanism of activation and function of protein kinase B," *Current Opinion in Genetics & Development* 8(1):55–62, Feb. 1998.
Bellacosa et al., "Molecular alterations of the AKT2 oncogene in ovarian and breast carcinomas," *International J. Cancer* 64(4):280–285, Aug. 22, 1995.
Boe, "A target for phosphoinositide 3–kinase: Akt/PKB," *Trends Biochem. Sci.* 20:441–442, Nov. 1995.
Cheng et al., "AKT2, a putative oncogene encoding a member of a subfamily of protein–serine/threonine kinases, is amplifed in human ovarian carcinomas," *P.N.A.S. U.S.A.* 89:9267–9271, Oct. 1992.
Cheng et al., "Amplification of AKT2 in human pancreatic cells and inhibition of AKT2 expression and tumorigenicity by antisense RNA," *P.N.A.S. U.S.A.* 93:3636–3641, Apr. 1996.
Coffer et al., "Protein kinase B (c–Akt): a multifunctional mediator of phosphatidylinositol 3–kinase activation," *Biochem. J.* 335:1–13, 1998.
Downward, "Mechanisms and consequences of activation of protein kinase B/Akt," *Current Opinion in Cell Biology* 10(2):262–267, Apr. 1998.
Nakatani et al., "Up–regulation of Akt3 in estrogen receptor–deficient breast cancers and androgen–independent prostate cancer lines," *J. Biol. Chem.* 274(31):21528–21532, Jul. 1999.
Staal, "Molecular cloning of the akt oncogene and its human homologues AKT1 and AKT2: amplification of AKT1 in a primary human gastric adenocarcinoma," *P.N.A.S. U.S.A.* 84(14):5034–5037, Jul. 1987.

* cited by examiner

*Primary Examiner*—Karen A. Lacourciere
(74) *Attorney, Agent, or Firm*—Jane E. R. Potter; Charlene A. Launer; Robert P. Blackburn

(57) ABSTRACT

Inhibitors of human Akt3, including antisense oligonucleotides, methods, and compositions specific for human Akt3, are provided. Methods of using the compositions for modulating Akt3 expression and for regulating cell growth, particularly tumor cell growth, are also provided.

5 Claims, 6 Drawing Sheets

Effect of AKT3 AS/RC on Growth of PC3

AKT3-AS/RC effect on proliferation of SKOV3 cells

Effect of Akt3 AS on Growth of MDA231

Effect of Akt1AS on Growth of MDA231 Cells

Figure 6

Human Akt3 polynucleotide sequence

```
   1 gggagtcatc atgagcgatg ttaccattgt gaaagaaggt tgggttcaga agaggggaga
  61 atatataaaa aactggaggc caagatactt cctttttgaag acagatggct cattcatagg
 121 atataaagag aaacctcaag atgtggattt acctatccc ctcaacaact tttcagtggc
 181 aaaatgccag ttaatgaaaa cagaacgacc aaagccaaac acatttataa tcagatgtct
 241 ccagtggact actgttatag agagaacatt tcatgtagat actccagagg aaagggaaga
 301 atggacagaa gctatccagg ctgtagcaga cagactgcag aggcaagaag aggagagaat
 361 gaattgtagt ccaacttcac aaaattgataa tataggagag gaagagatgg atgcctctac
 421 aacccatcat aaaagaaaga caatgaatga ttttgactat tgaaactac taggtaaagg
 481 cacttttggg aaagttattt tggttcgaga gaaggcaagt ggaaaatact atgctatgaa
 541 gattctgaag aaagaagtca ttattgcaaa ggatgaagtg gcacacactc taactgaaag
 601 cagagtatta aagaacacta gacatccctt tttaacatcc ttgaaatatt ccttccagac
 661 aaaagaccgt ttgtgttttg tgatggaata tgttaatggg ggcgagctgt ttttccattt
 721 gtcgagagag cgggtgttct ctgaggaccg cacacgtttc tatggtcag aaattgtctc
 781 tgccttggac tatctacatt ccggaaagat tgtgtaccgt gatctcaagt tggagaatct
 841 aatgctggac aaagatggcc acataaaaat tacagatttt ggactttgca agaagggat
 901 cacagatgca gccaccatga agacattctg tggcactcca gaatatctgg caccagaggt
 961 gttagaagat aatgactatg gccgagcagt gactggtgg ggcctagggg ttgtcatgta
1021 tgaaatgatg tgtgggaggt tacctttcta caaccaggac catgagaaac ttttgaatt
1081 aatattaatg gaagacatta aatttcctcg aacactctct tcagatgcaa aatcattgct
1141 ttcagggctc ttgataaagg atccaaataa acgccttggt ggaggaccag atgatgcaaa
1201 agaaattatg agacacagtt tcttctctgg agtaaactgg caagatgtat atgataaaaa
1261 gcttgtacct ccttttaaac ctcaagtaac atctgagaca gatactagat attttgatga
1321 agaatttaca gctcagacta ttacaataac accacctgaa aaatatgatg aggatggtat
1381 ggactgcatg gacaatgaga ggcggccgca tttccctcaa ttttcctact ctgcaagtgg
1441 acgagaataa gtctctttca ttctgctact tcactgtcat cttcaattta ttactgaaaa
1501 tgattcctgg acatcaccag tcctagctct tacacatagc aggggca
```

AKT3 INHIBITORS

CROSS-REFERENCE TO RELATED APPLICATIONS

This application claims priority from U.S. Provisional Patent Application No. 60/203,543 filed May 10, 2000, which is incorporated by reference herein in its entirety.

TECHNICAL FIELD

The present invention provides methods and compositions for modulating the expression of Akt3, and antisense and ribozyme compounds specifically hybridizable with Akt3.

BACKGROUND OF THE INVENTION

Akt3 is one of three serine/threonine protein kinases implicated in mediating apoptosis, stimulating cell growth, and regulating other biological responses. Akt1 and Akt2 are also within this group. (Coffer, P. J. et al., *Biochem. J.* 335:1–13, 1998.) Studies have suggested a role of Akt1 and Akt2 in cancer. For example, gene amplification resulted in increased Akt2 protein and mRNA in several cancers. (Staal, S. P. et al., *P.N.A.S.* 84:5034–5037, 1987; Cheng, J. Q. et al., *P.N.A.S.* 93:3636–3641, 1996; Cheng, J. et al., *P.N.A.S.* 89:9267–9271.)

Due to its potential role in cancer, there is a need in the art for compositions and methods that regulate expression and/or function of each Akt protein, including Akt3.

SUMMARY OF THE INVENTION

The present invention provides, in one embodiment, inhibitors of Akt3. Inventive inhibitors include, but are not limited to, antisense molecules, ribozymes, antibodies or antibody fragments, proteins or polypeptides as well as small molecules. Exemplary antisense molecules comprise at least 10, 15 or 20 consecutive nucleotides of or hybridize under stringent conditions to the nucleic acid of SEQ ID NO:1. More preferred are antisense molecules that comprise at least 25 consecutive nucleotides of or hybridize under stringent conditions to the sequence of SEQ ID NO:1. Representative antisense molecules are provided herein as SEQ ID NOS:2–6 and 12–19.

In further embodiments, compositions are provided that comprise one or more Akt3 inhibitor in a pharmaceutically acceptable carrier.

Additional embodiments provide methods of decreasing Akt3 gene expression or biological activity.

The invention provides an antisense oligonucleotide comprising at least one modified internucleoside linkage.

The invention further provides an antisense oligonucleotide having a phosphorothioate linkage.

The invention still further provides an antisense oligonucleotide comprising at least one modified sugar moiety.

The invention also provides an antisense oligonucleotide comprising at least one modified sugar moiety which is a 2'-O-methoxyethyl sugar moiety.

The invention further provides an antisense oligonucleotide comprising at least one modified nucleobase.

The invention still further provides an antisense oligonucleotide having a modified nucleobase wherein the modified nucleobase is 5-methylcytosine.

The invention also provides an antisense compound wherein the antisense compound is a chimeric oligonucleotide.

The invention provides a method of inhibiting the expression of human Akt3 in human cells or tissues comprising contacting the cells or tissues in vivo with an antisense compound or a ribozyme of 8 to 35 nucleotides in length targeted to a nucleic acid molecule encoding human Akt3 so that expression of human Akt3 is inhibited.

The invention further provides a method of modulating growth of cancer cells comprising contacting the cancer cells in vivo with an antisense compound or ribozyme of 8 to 35 nucleotides in length targeted to a nucleic acid molecule encoding human Akt3 so that expression of human Akt3 is inhibited.

The invention still further provides for identifying target regions of Akt3 polynucleotides. The invention also provides labeled probes for identifying Akt3 polynucleotides by in situ hybridization.

The invention provides for the use of an Akt3 inhibitor according to the invention to prepare a medicament for modulating cell proliferation.

The invention also provides a pharmaceutical composition for inhibiting expression of the Akt3, comprising an antisense oligonucleotide according to the invention in admixture with a physiologically acceptable carrier or diluent.

The invention further provides a ribozyme capable of specifically cleaving Akt3 RNA, and a pharmaceutical composition comprising the ribozyme.

The invention also provides small molecule inhibitors of Akt3 wherein the inhibitors are capable of reducing the activity of Akt3 or of reducing or preventing the expression of Akt3 mRNA.

BRIEF DESCRIPTION OF THE DRAWINGS

FIG. 6 is an Akt3 polynucleotide (SEQ ID NO:1).

DETAILED DESCRIPTION OF THE INVENTION

Introduction

Figure 1:
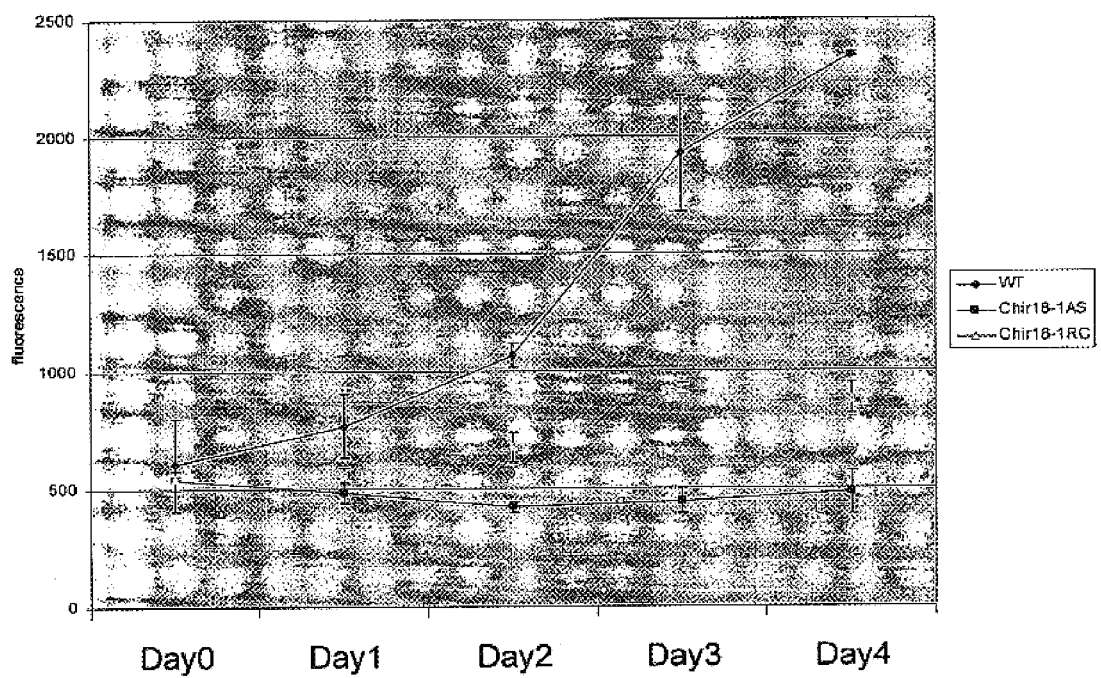
FIG. 1 is a graph depicting the effect of Akt3 antisense oligonucleotides on growth of PC3 cells.

The invention relates to the use of inhibitors, preferably oligonucleotides, such as antisense molecules or ribozymes, to target and modulate the expression of polynucleotides comprising an Akt3 nucleotide sequence. Akt3 is a member of the family of serine/threonine protein kinases, also known as protein kinase B. To date, three mammalian isoforms of Akt have been identified and are designated Akt1, Akt2 and Akt3.

As discussed further below, several lines of evidence point to a role of Akt in cancer. Akt1 is a cellular homolog of a viral oncogene that causes leukemia in mice. (Staal, S. P. et al., *P.N.A.S.* 84:5034–5037, 1987.) Both Akt1 and Akt2 are overexpressed in various mammalian cancers, including gastric adenocarcinomas (Akt1) and breast, ovarian and pancreatic cancers. (Staal, S. P. et al., *P.N.A.S.* 84:5034–5037, 1987; Cheng, J. Q. et al., *P.N.A.S.* 93:3636–3641, 1996; Cheng, J. et al., *P.N.A.S.* 89:9267–9271.) Recently, Akt3 enzymatic activity and mRNA levels were found to be elevated in breast cancer cells lines and tumors that lack the estrogen receptor. The levels were also raised in androgen-insensitive prostate cancer cell lines. (Nakatani, K. et al., *J. Biol. Chem.* 274:21528–21532, 1999.) However, prior to the present invention, there was no evidence that inhibition of Akt3 expression or activity would have an effect on tumor cell growth or viability.

Akt8 refers to a retrovirus isolated from the AKR strain of mice; a non-viral DNA component was later identified in mice. Two human homologs, Akt1 and Akt2, were cloned and mapped to a region of chromosome 14 that is often affected by translocations and inversions in human T-cell leukemia and lymphoma and other T-cell proliferation conditions. (Coffer, P. J. et al., *Biochem. J.* 335:1–13, 1998.)

Akt1 is also known as PKBα and RAC-PKα, and is involved in signaling pathways. Akt1 is found in the cytosol, and translocates to the plasma membrane when the cell is stimulated by platelet derived growth factor, epidermal growth factor, basic fibroblast growth factor, stresses such as heat or hyperosmolarity, and insulin. (Bos, *Trends Biochem. Sci.* 20:441–442, 1995.) After translocation to the plasma membrane, Akt1 can mediate a variety of cellular fates, including apoptosis, response to insulin, differentiation, proliferation, protein synthesis, and response to stress. (Alessi et al., *Curr. Opin. Genet. Dev.* 8:55–62, 1998; Downward, *Curr. Opin. Cell Biol.* 10:262–267, 1998.)

The role of Akt1 in preventing apoptosis may relate to the overexpression of Akt1 in some human cancers, including 3% of breast cancers (Bellacosa et al., *Int. J. Cancer* 64:280–285, 1995) and other cancers (Staal, S. P. et al., *P.N.A.S.* 84:5034–5037, 1987). Akt1 may help to protect cells from agents that would otherwise stimulate apoptosis. Higher expression of Akt1 in cancer cells may allow preferential survival while other cells undergo normal programmed cell death in response to such agents.

Akt1 is a potential target for cancer therapeutics including antisense oligonucleotides. U.S. Pat. No. 5,958,773 discloses the use of phosphorothioate oligodeoxynucleotides to inhibit Akt1 mRNA expression in tumor cell lines. Several antisense sequences yielded at least 35% inhibition of Akt1 expression. However, the patent does not disclose an effect on cell viability.

Akt2 overexpression may contribute to the malignant phenotype of some human pancreatic cancers. Two pancreatic cell lines, ASPC1 and PANC1, showed 30-fold and 50-fold amplification of Akt2, as well as increased Akt2 transcript levels. Pancreatic cells transfected with antisense constructs targeted to Akt2 showed lower density of growth in vitro than non-transfected or control-transfected cells. The antisense treatment blocked expression of Akt2 protein. PANC1 cells transfected with antisense RNA exhibited reduced ability to produce tumors in nude mice, compared with cells transfected with sense constructs. (Cheng, J. Q. et al., *P.N.A.S.* 93:3636–3641, 1996.) The results discussed above relate to modulating Akt1 and Akt2 expression. The present invention helps to elucidate the roles of Akt in cancer, by disclosing for the first time that antisense constructs targeting Akt3 can inhibit growth of ovarian, prostate, and breast cancer cells.

Oligonucleotides for Targeting Akt3 Polynucleotides

According to the present invention, oligonucleotide molecules capable of hybridizing with Akt3 polynucleotides inhibited the proliferation of ovarian, prostate and breast cancer cell lines. These cell lines are all standard models for cancer cell proliferation and growth in vivo, and the results support in vivo use of the Akt3 antisense molecules to ameliorate cancer in humans and other mammals. MDA231 is an estrogen receptor-negative cell line with high metastatic potential. PC3 is an androgen receptor-negative cell line.

Included within the scope of the invention are oligonucleotides capable of hybridizing with Akt3 DNA or RNA, referred to as the target polynucleotide. An oligonucleotide need not be 100% complementary to the target polynucleotide, as long as specific hybridization is achieved. The degree of hybridization to be achieved is that which interferes with the normal function of the target polynucleotide, be it transcription, translation, pairing with a complementary sequence, or binding with another biological component such as a protein. An antisense oligonucleotide can interfere with DNA replication and transcription, and it can interfere with RNA translocation, translation, splicing, and catalytic activity.

The invention includes within its scope any oligonucleotide of about 8 to about 35 nucleotides in length, including variations as described herein, wherein the oligonucleotide hybridizes to a Akt3 polynucleotide, including DNA or mRNA, such that an effect on the normal function of the polynucleotide is achieved. The nucleotide sequence of Akt3 is shown in FIG. 6 (SEQ ID NO:1). Preferred antisense oligonucleotides include:

P0703: CGACAAATGGAAAAACAGCTCGCC (SEQ ID NO:2)

P1550: TGGCTGGTCTGGGATGTCGGAAGG (SEQ ID NO:3)

P1674: ACAGTAGCAGCAACAGCATGAGACC (SEQ ID NO:4)

P0197: TTTGGCTTTGGTCGTTCGTTCTGTTTTCA (SEQ ID NO:5)

P0987: CCCTAGGCCCCACCAGTCTACTGCT (SEQ ID NO:6)

P687: ACAGCTCGCCCCCATTAACATATTC (SEQ ID NO:12)

P714: CACCCGCTCTCTCGACAATGGA (SEQ ID NO:13)

P720: GAGAACACCCGCTCTCTCGCAAA (SEQ ID NO:14)

P737: AACGTGTGCGGTCCTCAGAGACA (SEQ ID NO:15)

P768: GTCCAAGGCAGAGCAATTTCTGCA (SEQ ID NO.16)

P812: CTCCAACTTGGAATCACGGTACACA (SEQ ID NO:17)

P842: TTATTGTGGCCATCTTTGTCCAGCAT (SEQ ID NO:18)

P890: GCTCGATCTGTGATCCCTTCTTTGC (SEQ ID NO:19)

The antitumor use of the oligonucleotides disclosed herein is based on the discovery that Akt3 antisense oligonucleotides can reduce Akt3 mRNA levels in tumor cells, and can inhibit proliferation of cells of three separate tumor cell lines. To measure the effect on mRNA, SW620 cells were incubated with a transfection mixture of an oligonucleotide and a carrier, specifically a lipitoid or cholesteroid, although other carriers can be used as is known in the art. After an incubation of 2–24 hours, the transfection mixture was removed and replaced with normal growth media as described in the Examples.

Figure 5:
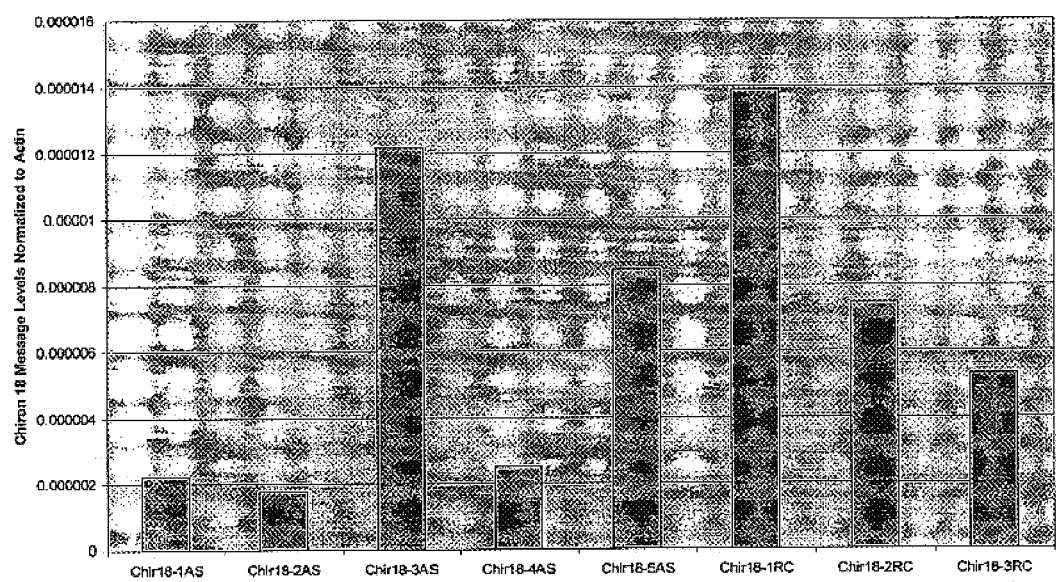
FIG. 5 is a bar graph depicting levels of Akt3 mRNA in SKOV3 cells treated with antisense and sense Akt3 oligonucleotides.

Total RNA was extracted from the cells, reverse transcribed, and amplified as described in the Examples. As shown in FIG. 5, incubation with antisense oligonucleotides (SEQ ID NOS:2–6) reduced the Akt3 mRNA levels relative to actin in SW620 cells. The greatest reduction was achieved with SEQ ID NOS:2, 3, and 5.

Figure 2:
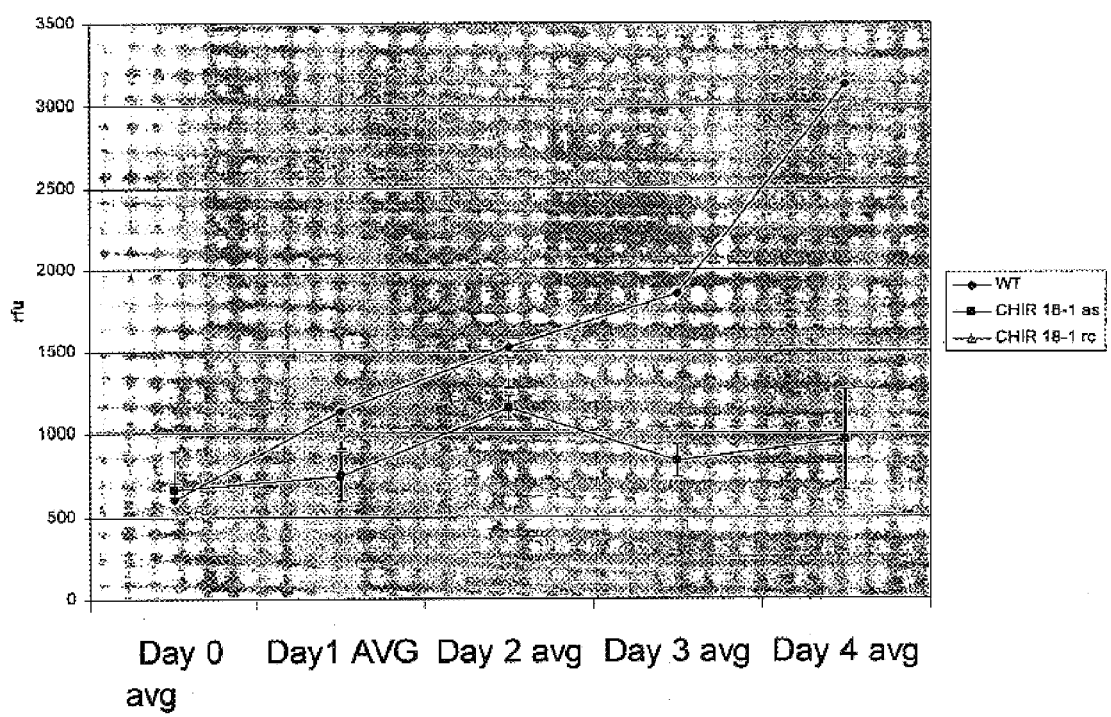
FIG. 2 is a graph depicting the effect of Akt3 antisense oligonucleotides on proliferation of SKOV3 cells.
Figure 3:
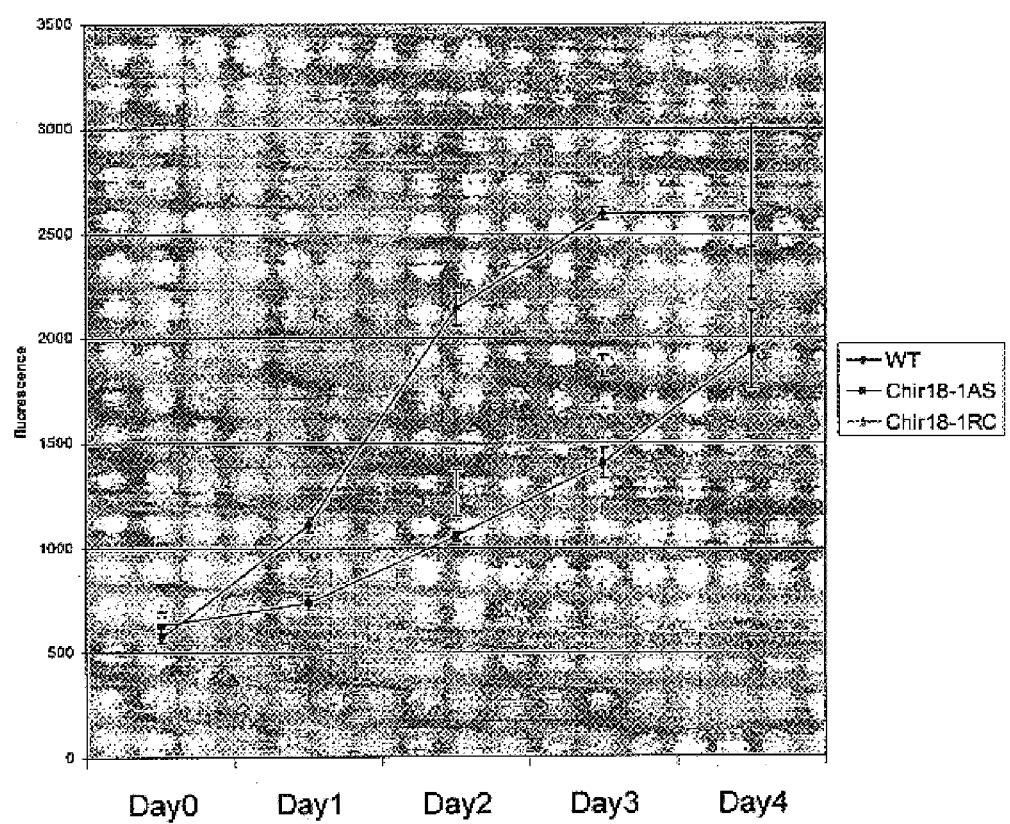
FIG. 3 is a graph depicting the effect of Akt3 antisense oligonucleotides on growth of MDA231 cells.
Figure 4:
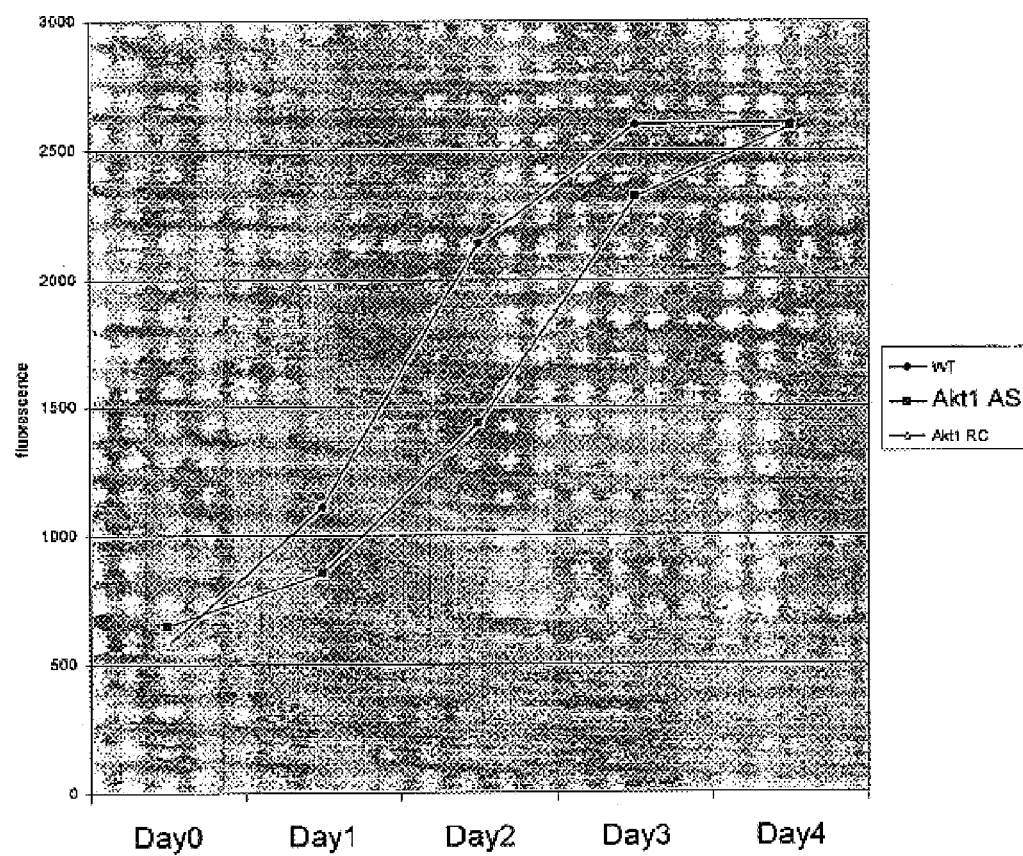
FIG. 4 is a graph depicting the effect of an Akt1 antisense oligonucleotide on growth of MDA231 cells.

SEQ ID NO:2 was selected for determining whether the reduction in Akt3 mRNA correlated with an effect on cell growth. Cells of tumor cell lines PC3, SKOV3, and MDA231 were transfected with antisense oligonucleotide (SEQ ID NO:2) as described in Example 1. On each day of the proliferation assay, medium was removed from one of five separate plates for each cell line, and on day four all plates were treated to determine the number of cells in each well of the 96-well plates. Results were averaged and plotted (FIGS. 1–3). As shown in FIG. 1, SEQ ID NO:1 completely inhibited proliferation of prostate PC3 cells at each of the four timepoints, whereas untreated cells continued to proliferate. SKOV3 (ovary) cells exhibited a minor degree of proliferation; at day 4, cell numbers had not doubled in the treated group, whereas they increased over 6-fold in the untreated group (FIG. 2). Treated MDA231 cells exhibited lower proliferation rates than untreated cells (FIG. 3). In contrast, antisense oligonucleotide directed against Akt1 had no effect on cell proliferation in MDA231 cells at day 4.

Examples of preferred antisense compounds useful in the invention are based on SEQ ID NOS:2–6 and 12–19, most preferably SEQ ID NO:2 and 16, and include oligonucleotides containing modified backbones or non-natural internucleoside linkages. Oligonucleotides having modified backbones include those retaining a phosphorus atom in the backbone, and those that do not have a phosphorus atom in the backbone. Preferred modified oligonucleotide backbones include phosphorothioates, chiral phorphorothioates, phosphotriesters, aminoalkylphosphotriesters, methyl and other alkyl phosphonates including 3'-alkylene phosphonates and chiral phosphonates, phosphinates, phosphoroamidates including 3'-anino phosphoroamidate and aminoalkyl-phosphoroamidates, thiooophosphoroamidates, thioalkylphosphonates, thionoalkyl-phosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid also included.

The present invention relates to antisense oligonucleotides designed to interfere with the normal function of Akt3 polynucleotides. Any modifications or variations of the antisense molecule which are known in the art to be broadly applicable to antisense technology are included within the scope of the invention. Such modifications include preparation of phosphorus-containing linkages as disclosed in U.S. Pat. No. 5,536,821; 5,541,306; 5,550,111; 5,563,253; 5,571,799; 5,587,361, 5,625,050 and 5,958,773. The '773 patent relates to antisense compounds for modulating Akt1 expression, and therefore has particular relevance to modifications that can be made to the present Akt3 antisense compounds.

The antisense compounds of the invention can include modified bases as disclosed in 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567, 810, 5,574,142, 5,585,481, 5,587,371, 5,597,696 and 5,958, 773.

Chimeric antisense oligonucleotides are also within the scope of the invention, and can be prepared from the present inventive oligonucleotides using the methods described in, for example, U.S. Pat. Nos. 5,013,830, 5,149,797, 5,403, 711, 5,491,133, 5,565,350, 5,652,355, 5,700,922 and 5,958, 773.

The experiments discussed herein used antisense oligonucleotide P0703 (SEQ ID NO:2). Additional Akt3 antisense oligonucleotides are also useful in the practice of the invention, including SEQ ID NOS:3–6 and 12–19. Preferred antisense oligonucleotides in addition to those of SEQ ID NO:2–6 and 12–19 can be selected by routine experimentation using, for example, assays described in the Examples. Although the inventors are not bound by a particular mechanism of action, it is believed that the antisense oligonucleotides achieve an inhibitory effect by binding to a complementary region of the target polynucleotide within the cell using Watson-Crick base pairing. Where the target polynucleotide is RNA, experimental evidence indicates that the RNA component of the hybrid is cleaved by RNase H (Giles, R. V. et al., *Nuc. Acids Res.* 23:954–961, 1995; U.S. Pat. No. 6,001,653). Generally, a hybrid containing 10 base pairs is of sufficient length to serve as a substrate for RNase H. However, to achieve specificity of binding, it is preferable to use an antisense molecule of at least 17 nucleotides, as a sequence of this length is likely to be unique among human genes.

As disclosed in U.S. Pat. No. 5,998,383, incorporated herein by reference, the oligonucleotide is selected such that the sequence exhibits suitable energy related characteristics important for oligonucleotide duplex formation with their complementary templates, and shows a low potential for self-dimerization or self-complementation (Anazodo et al., *Biochem. Biophys. Res. Commun.* 229:305–309, 1996). The computer program OLIGO (Primer Analysis Software, Version 3.4), is used to determined antisense sequence melting temperature, free energy properties, and to estimate potential self-dimer formation and self-complimentarity properties. The program allows the determination of a qualitative estimation of these two parameters (potential self-dimer formation and self-complimentary) and provides an indication of "no potential" or "some potential" or "essentially complete potential." Segments of Akt3 polynucleotides are generally selected that have estimates of no potential in these parameters. However, segments can be used that have "some potential" in one of the categories. A balance of the parameters is used in the selection.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. According to the invention, this experimentation can be performed routinely by transfecting cells with an antisense oligonucleotide using methods described in Example 1. mRNA levels in the cell can be measured routinely in treated and control cells by reverse transcription of the mRNA and assaying the cDNA levels. The biological effect can be determined routinely by measuring cell growth or viability as is known in the art.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A.

D., *T.I.B.S.* 23:45–50, 1998.) According to the present invention, cultures of SW620 cells were transfected with five different antisense oligonucleotides designed to target Akt3. These oligonucleotides are shown in SEQ ID NO:2–6 and 12–19. The levels of mRNA corresponding to Akt3 were measured in treated and control cells. SEQ ID NO:2, 3 and 5 caused dramatic decreases in Akt3 mRNA when normalized to actin mRNA levels. SEQ ID NO:4 and 6 also caused decreased mRNA levels but the decreases were not as extensive as with SEQ ID NO:2, 3 and 5.

Additional inhibitors include ribozymes, proteins or polypeptides, antibodies or fragments thereof as well as small molecules. Each of these Akt3 inhibitors share the common feature in that they reduce the expression and/or biological activity of Akt3. In addition to the exemplary Akt3 inhibitors disclosed herein, alternative inhibitors may be obtained through routine experimentation utilizing methodology either specifically disclosed herein or as otherwise readily available to and within the expertise of the skilled artisan.

Ribozymes

Akt3 inhibitors may be ribozymes. A ribozyme is an RNA molecule that specifically cleaves RNA substrates, such as mRNA, resulting in specific inhibition or interference with cellular gene expression. As used herein, the term ribozymes includes RNA molecules that contain antisense sequences for specific recognition, and an RNA-cleaving enzymatic activity. The catalytic strand cleaves a specific site in a target RNA at greater than stoichiometric concentration.

A wide variety of ribozymes may be utilized within the context of the present invention, including for example, the hammerhead ribozyme (for example, as described by Forster and Symons, *Cell* 48:211–220 (1987); Haseloff and Gerlach, *Nature* 328:596–600 (1988); Walbot and Bruening, *Nature* 334:196 (1988); Haseloff and Gerlach, *Nature* 334:585 (1988)); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). According to certain embodiments of the invention, any such Akt3 mRNA-specific ribozyme, or a nucleic acid encoding such a ribozyme, may be delivered to a host cell to effect inhibition of Akt3 gene expression. Ribozymes and the like may therefore be delivered to the host cells by DNA encoding the ribozyme linked to a eukaryotic promoter, such as a eukaryotic viral promoter, such that upon introduction into the nucleus, the ribozyme will be directly transcribed.

Proteins and Polypeptides

In addition to the antisense molecules and ribozymes disclosed herein, Akt3 inhibitors of the present invention also include proteins or polypeptides that are effective in either reducing Akt3 gene expression or in decreasing one or more of Akt3's biological activities. A variety of methods are readily available in the art by which the skilled artisan may, through routine experimentation, rapidly identify such Akt3 inhibitors. The present invention is not limited by the following exemplary methodologies.

As discussed above, Akt3 is an active protein kinase that mediates apoptosis. Thus, inhibitors of Akt3's biological activities encompass those proteins and/or polypeptides that interfere with Akt3's kinase activity. Such interference may occur through direct interaction with Akt3's kinase domain or indirectly through non- or un-competitive inhibition such as via binding to an allosteric site. Accordingly, available methods for identifying proteins and/or polypeptides that bind to Akt3 may be employed to identify lead compounds that may, through the methodology disclosed herein, be characterized for their Akt3 inhibitory activity.

A vast body of literature is available to the skilled artisan that describes methods for detecting and analyzing protein-protein interactions. Reviewed in Phizicky, E. M. et al., *Microbiological Reviews* 59:94–123 (1995) incorporated herein by reference. Such methods include, but are not limited to physical methods such as, e.g., protein affinity chromatography, affinity blotting, immunoprecipitation and cross-linking as well as library-based methods such as, e.g., protein probing, phage display and two-hybrid screening. Other methods that may be employed to identify protein-protein interactions include genetic methods such as use of extragenic suppressors, synthetic lethal effects and unlinked noncomplementation. Exemplary methods are described in further detail below.

Inventive Akt3 inhibitors may be identified through biological screening assays that rely on the direct interaction between the Akt3 protein and a panel or library of potential inhibitor proteins. Biological screening methodologies, including the various "n-hybrid technologies," are described in, for example, Vidal, M. et al., *Nucl. Acids Res.* 27(4):919–929 (1999); Frederickson, R. M., *Curr. Opin. Biotechnol.* 9(1):90–6 (1998); Brachmann, R. K. et al., *Curr. Opin. Biotechnol.* 8(5):561–568 (1997); and White, M. A., *Proc. Natl. Acad. Sci. U.S.A.* 93:10001–10003 (1996) each of which is incorporated herein by reference.

The two-hybrid screening methodology may be employed to search new or existing target cDNA libraries for Akt3 binding proteins that have inhibitory properties. The two-hybrid system is a genetic method that detects protein-protein interactions by virtue of increases in transcription of reporter genes. The system relies on the fact that site-specific transcriptional activators have a DNA-binding domain and a transcriptional activation domain. The DNA-binding domain targets the activation domain to the specific genes to be expressed. Because of the modular nature of transcriptional activators, the DNA-binding domain may be severed covalently from the transcriptional activation domain without loss of activity of either domain. Furthermore, these two domains may be brought into juxtaposition by protein-protein contacts between two proteins unrelated to the transcriptional machinery. Thus, two hybrids are constructed to create a functional system. The first hybrid, i.e., the bait, consists of a transcriptional activator DNA-binding domain fused to a protein of interest. The second hybrid, the target, is created by the fusion of a transcriptional activation domain with a library of proteins or polypeptides. Interaction between the bait protein and a member of the target library results in the juxtaposition of the DNA-binding domain and the transcriptional activation domain and the consequent up-regulation of reporter gene expression.

A variety of two-hybrid based systems are available to the skilled artisan that most commonly employ either the yeast Gal4 or *E. coli* LexA DNA-binding domain (BD) and the yeast Gal4 or herpes simplex virus VP16 transcriptional activation domain. Chien, C.-T. et al., *Proc. Natl. Acad. Sci. U.S.A.* 88:9578–9582 (1991); Dalton, S. et al., *Cell* 68:597–612 (1992); Durfee, T. K. et al., *Genes Dev.* 7:555–569 (1993); Vojtek, A. B. et al., *Cell* 74:205–214 (1993); and Zervos, A. S. et al., *Cell* 72:223–232 (1993). Commonly used reporter genes include the *E. coli* lacZ gene as well as selectable yeast genes such as HIS3 and LEU2. Fields, S. et al., *Nature* (London) 340:245–246 (1989); Durfee, T. K., supra; and Zervos, A. S., supra. A wide variety of activation domain libraries is readily available in the art such that the screening for interacting proteins may be performed through routine experimentation.

Suitable bait proteins for the identification of Akt3 interacting proteins may be designed based on the Akt3 cDNA sequence presented herein as SEQ ID NO:1. Such bait proteins include either the full-length Akt3 protein or fragments thereof.

Plasmid vectors, such as, e.g., pBTM116 and pAS2-1, for preparing Akt3 bait constructs and target libraries are readily available to the artisan and may be obtained from such commercial sources as, e.g., Clontech (Palo Alto, Calif.), Invitrogen (Carlsbad, Calif.) and Stratagene (La Jolla, Calif.). These plasmid vectors permit the in-frame fusion of cDNAs with the DNA-binding domains as LexA or Gal4BD, respectively.

Akt3 inhibitors of the present invention may alternatively be identified through one of the physical or biochemical methods available in the art for detecting protein-protein interactions.

Through the protein affinity chromatography methodology, lead compounds to be tested as potential Akt3 inhibitors may be identified by virtue of their specific retention to Akt3 when either covalently or non-covalently coupled to a solid matrix such as, e.g., Sepharose beads. The preparation of protein affinity columns is described in, for example, Beeckmans, S. et al., *Eur. J. Biochem.* 117:527–535 (1981) and Formosa, T. et al., *Methods Enzymol* 208:2445 (1991). Cell lysates containing the full complement of cellular proteins may be passed through the Akt3 affinity column. Proteins having a high affinity for Akt3 will be specifically retained under low-salt conditions while the majority of cellular proteins will pass through the column. Such high affinity proteins may be eluted from the immobilized Akt3 under conditions of high-salt, with chaotropic solvents or with sodium dodecyl sulfate (SDS). In some embodiments, it may be preferred to radiolabel the cells prior to preparing the lysate as an aid in identifying the Akt3 specific binding proteins. Methods for radiolabeling mammalian cells are well known in the art and are provided, e.g., in Sopta, M. et al., *J. Biol. Chem.* 260:10353–10360 (1985).

Suitable Akt3 proteins for affinity chromatography may be fused to a protein or polypeptide to permit rapid purification on an appropriate affinity resin. For example, the Akt3 cDNA may be fused to the coding region for glutathione S-transferase (GST) which facilitates the adsorption of fusion proteins to glutathione-agarose columns. Smith et al., *Gene* 67:31–40 (1988). Alternatively, fusion proteins may include protein A, which can be purified on columns bearing immunoglobulin G; oligohistidine-containing peptides, which can be purified on columns bearing $Ni^{2+}$; the maltose-binding protein, which can be purified on resins containing amylose; and dihydrofolate reductase, which can be purified on methotrexate columns. One exemplary tag suitable for the preparation of Akt3 fusion proteins that is presented herein is the epitope for the influenza virus hemagglutinin (HA) against which monoclonal antibodies are readily available and from which antibodies an affinity column may be prepared.

In those cases where candidate Akt3 inhibitors are directed against Akt3's kinase domain, it may be advantageous to phosphorylate the Akt3 protein prior to preparing the affinity column. Suitable phosphorylation conditions include 10 mM ATP, 1 mM DTT, 10 mM $MgCl_2$, 10 mM $MnCl_2$ and 50 mM Tris, pH 7.5.

Proteins that are specifically retained on an Akt3 affinity column may be identified after subjecting to SDS polyacrylamide gel electrophoresis (SDS-PAGE). Thus, where cells are radiolabeled prior to the preparation of cell lysates and passage through the Akt3 affinity column, proteins having high affinity for Akt3 may be detected by autoradiography. The identity of Akt3 specific binding proteins may be determined by protein sequencing techniques that are readily available to the skilled artisan, such as Mathews, C. K. et al., *Biochemistry*, The Benjamin/Cummings Publishing Company, Inc. pp.166–170 (1990).

Antibodies or Antibody Fragments

Akt3 inhibitors of the present invention include antibodies and/or antibody fragments that are effective in reducing Akt3 gene expression and/or biological activity. Suitable antibodies may be monoclonal, polyclonal or humanized monoclonal antibodies. Antibodies may be derived by conventional hybridoma based methodology, from antisera isolated from Akt3 inoculated animals or through recombinant DNA technology. Alternatively, inventive antibodies or antibody fragments may be identified in vitro by use of one or more of the readily available phage display libraries. Exemplary methods are disclosed herein.

In one embodiment of the present invention, Akt3 inhibitors are monoclonal antibodies that may be produced as follows. Akt3 protein may be produced, for example, by expression of Akt3 cDNA in a baculovirus based system. By this method, Akt3 cDNA or a fragment thereof is ligated into a suitable plasmid vector that is subsequently used to transfect Sf9 cells to facilitate protein production. In addition, it may be advantageous to incorporate an epitope tag or other moiety to facilitate affinity purification of the Akt3 protein. Clones of Sf9 cells expressing Akt3 are identified, e.g., by enzyme linked immunosorbant assay (ELISA), lysates are prepared and the Akt3 protein purified by affinity chromatography and the purified protein is injected, intraperitoneally, into BALB/c mice to induce antibody production. It may be advantageous to add an adjuvant, such as Freund's adjuvant, to increase the resulting immune response.

Serum is tested for the production of specific antibodies and spleen cells from animals having a positive specific antibody titer are used for cell fusions with myeloma cells to generate hybridoma clones. Supernatants derived from hybridoma clones are tested for the presence of monoclonal antibodies having specificity against Akt3. For a general description of monoclonal antibody methodology, See, e.g., Harlow and Lane, *Antibodies: A Laboratory Manual*, Cold Spring Harbor Laboratory (1988).

In addition to the baculovirus expression system, other suitable bacterial or yeast expression systems may be employed for the expression of Akt3 protein or polypeptides thereof. As with the baculovirus system, it may be advantageous to utilize one of the commercially available affinity tags to facilitate purification prior to inoculation of the animals. Thus, the Akt3 cDNA or fragment thereof may be isolated by, e.g., agarose gel purification and ligated in frame with a suitable tag protein such as 6-His, glutathione-S-transferase (GST) or other such readily available affinity tag. See, e.g., *Molecular Biotechnology: Principles and Applications of Recombinant DNA*, ASM Press pp. 160–161 (ed Glick, B. R. and Pasternak, J. J. 1998).

In other embodiments of the present invention, Akt3 inhibitors are humanized anti-Akt3 monoclonal antibodies. The phrase "humanized antibody" refers to an antibody derived from a non-human antibody—typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., *Nature* 321:522–525 (1986); Morrison et al., *Proc. Natl. Acad. Sci., U.S.A.*, 81:6851–6855 (1984); Morrison and Oi, *Adv. Immunol.*, 44:65–92 (1988); Verhoeyer et al., *Science* 239:1534–1536 (1988); Padlan, *Molec. Immun.* 28:489–498 (1991); Padlan, *Molec. Immunol.* 31(3):169–217 (1994); and Kettleborough, C. A. et al., *Protein Eng.* 4(7):773–83 (1991) each of which is incorporated herein by reference.

The phrase "complementarity determining region" refers to amino acid sequences which together define the binding affinity and specificity of the natural Fv region of a native immunoglobulin binding site. See, e.g, Chothia et al.,*J. Mol. Biol.* 196:901–917 (1987); Kabat et al., U.S. Dept. of Health and Human Services NIH Publication No. 91–3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which patents are incorporated herein by reference.

Humanized antibodies to Akt3 can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be is produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

In the present invention, Akt3 polypeptides of the invention and variants thereof are used to immunize a transgenic animal as described above. Monoclonal antibodies are made using methods known in the art, and the specificity of the antibodies is tested using isolated Akt3 polypeptides. The suitability of the antibodies for clinical use is tested by, for example, exposing SW620 cells to the antibodies and measuring cell growth. According to the invention, inhibition of Akt3 expression using antisense oligonucleotides specific for Akt3 polynucleotides causes an inhibition of anchorage-independent growth of a colon cancer cell line, SW620. The antisense oligonucleotides also inhibited the proliferation of a breast cancer cell line, MDA231, and SW620 cells. Human monoclonal antibodies specific for Akt3 or a variant or fragment thereof can be tested for their ability to inhibit proliferation, colony growth, or any other biological parameter indicative of control of tumor growth, migration, or metastasis, particularly tumor cells of epithelial origin. Such antibodies would be suitable for pre-clinical and clinical trials as pharmaceutical agents for preventing or controlling growth of cancer cells.

It will be appreciated that alternative Akt3 inhibitor antibodies may be readily obtained by other methods commonly known in the art. One exemplary methodology for identifying antibodies having a high specificity for Akt3 is the phage display technology.

Phage display libraries for the production of high-affinity antibodies are described in, for example, Hoogenboom, H. R. et al., *Immunotechnology* 4(1):1–20 (1998); Hoogenboom, H. R., *Trends Biotechnol.* 15:62–70 (1997) and McGuinness, B. et al., *Nature Bio. Technol.* 14:1149–1154 (1996) each of which is incorporated herein by reference. Among the advantages of the phage display technology is the ability to isolate antibodies of human origin that cannot otherwise be easily isolated by conventional hybridoma technology. Furthermore, phage display antibodies may be isolated in vitro without relying on an animal's immune system.

Antibody phage display libraries may be accomplished, for example, by the method of McCafferty et al., *Nature* 348:552–554 (1990) which is incorporated herein by reference. In short, the coding sequence of the antibody variable region is fused to the amino terminus of a phage minor coat protein (pIII). Expression of the antibody variable region-pIII fusion construct results in the antibody's "display" on the phage surface with the corresponding genetic material encompassed within the phage particle.

Akt3 protein suitable for screening a phage library may be obtained by, for example, expression in baculovirus Sf9 cells as described, supra. Alternatively, the Akt3 coding region may be PCR amplified using primers specific to the desired region of the Akt3 protein. For example, where the inhibitor is directed against Akt3's kinase domain, fragments may be amplified that encode the amino acid sequence flanking lysine 40 in the active site. As discussed above, the Akt3 protein may be expressed in *E. coli* or yeast as a fusion with one of the commercially available affinity tags.

The resulting fusion protein may then be adsorbed to a solid matrix, e.g., a tissue culture plate or bead. Phage expressing antibodies having the desired anti-Akt3 binding properties may subsequently be isolated by successive panning, in the case of a solid matrix, or by affinity adsorption to a Akt3 antigen column. Phage having the desired Akt3 inhibitory activities may be reintroduced into bacteria by infection and propagated by standard methods known to those skilled in the art. See Hoogenboom, H. R., *Trends Biotechnol.*, supra for a review of methods for screening for positive antibody-pIII phage.

Small Molecules

The present invention also provides small molecule Akt3 inhibitors that may be readily identified through routine application of high-throughput screening (HTS) methodologies. Reviewed by Persidis, A., *Nature Biotechnology* 16:488–489 (1998). HTS methods generally refer to those technologies that permit the rapid assaying of lead compounds, such as small molecules, for therapeutic potential. HTS methodology employs robotic handling of test materials, detection of positive signals and interpretation of data. Such methodologies include, e.g., robotic screening technology using soluble molecules as well as cell-based systems such as the two-hybrid system described in detail above.

A variety of cell line-based HTS methods are available that benefit from their ease of manipulation and clinical relevance of interactions that occur within a cellular context as opposed to in solution. Lead compounds may be identified via incorporation of radioactivity or through optical assays that rely on absorbance, fluorescence or luminescence as read-outs. See, e.g., Gonzalez, J. E. et al., *Curr. Opin. Biotechnol.* 9(6):624–631 (1998) incorporated herein by reference.

HTS methodology may be employed, e.g., to screen for lead compounds that block one of Akt3's biological activities. By this method, Akt3 protein may be immunoprecipitated from cells expressing the protein and applied to wells on an assay plate suitable for robotic screening. Individual test compounds may then be contacted with the immunoprecipitated protein and the effect of each test compound on Akt3 kinase activity assessed by, e.g., incubating in the presence of $\gamma$-$^{32}$P-ATP in a suitable buffer system, and measuring the incorporation of $^{32}$P.

Methods for Assessing the Efficacy of Akt3 Inhibitors

Lead molecules or compounds, whether antisense molecules or ribozymes, proteins and/or peptides, antibodies and/or antibody fragments or small molecules, that are identified either by one of the methods described herein or via techniques that are otherwise available in the art, may be further characterized in a variety of in vitro, ex vivo and in vivo animal model assay systems for their ability to inhibit Akt3 gene expression or biological activity. As discussed in further detail in the Examples provided below, Akt3 inhibitors of the present invention are effective in reducing Akt3 expression levels. Thus, the present invention further discloses methods that permit the skilled artisan to assess the effect of candidate inhibitors.

Candidate Akt3 inhibitors may be tested by administration to cells that either express endogenous Akt3 or that are made to express Akt3 by transfection of a mammalian cell with a recombinant Akt3 plasmid construct.

Effective Akt3 inhibitory molecules will be effective in reducing the levels of Akt3 mRNA as determined, e.g., by Northern blot or RT-PCR analysis. For a general description of these procedures, see, e.g., Sambrook et al., *Molecular Cloning: A Laboratory Manual* Cold Spring Harbor Press (1989) and *Molecular Biotechnology: Principles and Applications of Recombinant DNA*, ASM Press (ed. Glick, B. R. and Pasternak, J. J. 1998) incorporated herein by reference. The effectiveness of a given candidate antisense molecule may be assessed by comparison with a control "antisense" molecule known to have no substantial effect on Akt3 expression when administered to a mammalian cell. Exemplary control molecules include the Akt3 oligonucleotides disclosed in Example 2.

In alternate embodiments of the present invention, the effect of Akt3 inhibitors on the rate of DNA synthesis after challenge with a radiation or chemotherapeutic agent may be assessed by, e.g., the method of Young and Painter. *Hum. Genet.* 82:113–117 (1989). Briefly, culture cells may be incubated in the presence of $^{14}$C-thymidine prior to exposure to, e.g., X-rays. Immediately after irradiation, cells are incubated for a short period prior to addition of $^{3}$H-thymidine. Cells are washed, treated with perchloric acid and filtered (Whatman GF/C). The filters are rinsed with perchloric acid, 70% alcohol and then 100% ethanol; radioactivity is measured and the resulting $^{3}$H/$^{14}$C ratios used to determine the rates of DNA synthesis.

Akt3 inhibitors effective in reducing Akt3 gene expression by one or more of the methods discussed above may be further characterized in vivo for efficacy in one of the readily available animal model systems. Various animal model systems for study of cancer and genetic instability associated genes are disclosed in, for example, Donehower, L. A. *Cancer Surveys* 29:329–352 (1997) incorporated herein by reference.

Pharmaceutical Compositions

The antisense oligonucleotides and ribozymes of the present invention can be synthesized by any method known in the art for ribonucleic or deoxyribonucleic nucleotides. For example, the oligonucleotides can be prepared using solid-phase synthesis such as in an Applied Biosystems 380B DNA synthesizer. Final purity of the oligonucleotides is determined as is known in the art.

The antisense oligonucleotides identified using the methods of the invention modulate tumor cell proliferation. Therefore, pharmaceutical compositions and methods are provided for interfering with cell proliferation, preferably tumor cell proliferation, comprising contacting tissues or cells with one or more of antisense oligonucleotides identified using the methods of the invention. Preferably, an antisense oligonucleotide having one of SEQ ID NOS:2–6 and 12–19 is administered.

The Examples describe reducing proliferation of hormone-independent prostate and breast cancer cell lines, as well as an ovarian cell line. Thus, the antisense compositions are useful for treating tumors of the breast, cancer, and ovary, particularly if initial clinical investigation shows the tumors to be unresponsive to estrogen or androgen.

The methods and compositions may also be used to treat proliferative disorders including other forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, colon cancer, pancreatic cancer, head and neck cancers, and nervous system cancers, benign lesions such as papillomas, arthrosclerosis, psoriasis, primary and secondary polythemia, mastocytosis, autoimmune diseases, angiogenesis, bacterial infections, and viral infections, such as HIV infections, hepatitis or herpes infections.

The invention provides pharmaceutical compositions of antisense oligonucleotides and ribozyrnes complementary to the Akt3 mRNA gene sequence as active ingredients for therapeutic application. These compositions can also be used in the method of the present invention. Where required the compounds are nuclease resistant. In general the pharmaceutical composition for modulating cell proliferation or for cytotoxicity in a mammal includes an effective amount of at least one antisense oligonucleotide as described above needed for the practice of the invention, or a fragment thereof shown to have the same effect, and a pharmaceutically physiologically acceptable carrier or diluent.

In one embodiment of the invention, a method is provided for reducing metastasis in a subject comprising administering an amount of an antisense oligonucleotide of the invention effective to reduce metastasis. Most preferably the antisense oligonucleotide is one of SEQ ID NOS:2–6 and 12–19.

The pharmaceutical composition for inhibiting tumorigenicity of neoplastic cells in a mammal consists of an effective amount of at least one active ingredient selected from antisense oligonucleotides complementary to the Akt3 mRNA, including the entire Akt3 mRNA or having short sequences as set forth in SEQ ID NOS:2–6 and 12–19 and a pharmaceutically physiologically acceptable carrier or diluent. Combinations of the active ingredients can be used.

The compositions can be administered orally, subcutaneously or parenterally including intravenous, intraarterial, intramuscular, intraperitoneally, and intranasal administration as well as intrathecal and infusion techniques as required by the malignant cells being treated. For delivery within the CNS intrathecal delivery can be used with for example an Ommaya reservoir or other methods known in the art. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids may also be included in the composition to facilitate oligonucleotide uptake. Implants of the compounds are also useful. In general the pharmaceutical compositions are sterile.

In the method of the present invention, proliferating cells including neoplastic cells are contacted with a growth inhibiting amount of the bioactive antisense oligonucleotide for the Akt3 mRNA or a fragment thereof shown to have substantially the same effect. In an embodiment the mammal to be treated is human but other mammalian species can be treated in veterinary applications.

By bioactive (expressible) is meant that the oligonucleotide is biologically active in the cell when delivered directly to the cell and/or is expressed by an appropriate promotor and active when delivered to the cell in a vector as described below. Nuclease resistance is provided by any method known in the art that does not substantially interfere with biological activity as described herein.

"Contacting the cell" refers to methods of exposing or delivery to a cell of antisense oligonucleotides whether directly or by viral or non-viral vectors and where the antisense oligonucleotide is bioactive upon delivery. The method of delivery will be chosen for the particular cancer being treated. Parameters that affect delivery can include the cell type affected and tumor location as is known in the medical art.

The treatment generally has a length proportional to the length of the disease process and drug effectiveness and the patient species being treated. It is noted that humans are treated generally longer than the Examples exemplified herein, which treatment has a length proportional to the length of the disease process and drug effectiveness. The doses may be single doses or multiple doses as determined by the medical practitioners and treatment courses will be repeated as necessary until diminution of the disease is achieved. Optimal dosing schedules may be calculated using measurements of drug accumulation in the body. Practitioners of ordinary skill in the art can readily determine optimum dosages, dosing methodologies, and repetition rates. Optimum dosages may vary depending on the relative potency of the antisense oligonucleotide, and can generally be determined based on values in in vitro and in vivo animal studies and clinical trials. Variations in the embodiments used may also be utilized. The amount must be effective to achieve improvement including but not limited to decreased tumor growth, or tumor size reduction or to improved survival rate or length or decreased drug resistance or other indicators as are selected as appropriate measures by those skilled in the art.

Although some antisense oligonucleotides may not completely abolish tumor cell growth in vitro, these antisense compounds may be clinically useful if they inhibit tumor growth enough to allow complementary treatments, such as chemotherapy, to be effective. The pharmaceutical compositions of the present invention therefore are administered singly or in combination with other drugs, such as cytotoxic agents, immunotoxins, alkylating agents, anti-metabolites, antitumor antibiotics and other anti-cancer drugs and treatment modalities that are known in the art. The composition is administered and dosed in accordance with good medical practice taking into account the clinical condition of the individual patient, the site and method of administration, scheduling of administration, and other factors known to medical practitioners. The "effective amount" for growth inhibition is thus determined by such considerations as are known in the art. The pharmaceutical composition may contain more than one embodiment of the present invention.

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell. Generally the construct contains the proper regulatory sequence or promotor to allow the sequence to be expressed in the targeted cell.

Once the oligonucleotide sequences are ready for delivery they can be introduced into cells as is known in the art. Transfection, electroporation, fusion, liposomes, colloidal polymeric particles and viral vectors as well as other means known in the art may be used to deliver the oligonucleotide sequences to the cell. The method selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

The present invention provides vectors comprising an expression control sequence operatively linked to the oligonucleotide sequences of the invention. The present invention further provides host cells, selected from suitable eucaryotic and procaryotic cells, which are transformed with these vectors as necessary. Such transformed cells allow the study of the function and the regulation of malignancy and the treatment therapy of the present invention.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al., *BioTechniques* 4:504–512 (1986) and include, for example, stable or transient transfection, lipofection, electroporation and infection with recombinant viral vectors.

Recombinant methods known in the art can also be used to achieve the antisense inhibition of a target nucleic acid. For example, vectors containing antisense nucleic acids can be employed to express an antisense message to reduce the expression of the target nucleic acid and therefore its activity.

The present invention also provides a method of evaluating if a compound inhibits transcription or translation of an Akt3 gene and thereby modulates (i.e., reduces) cell proliferation comprising transfecting a cell with an expression vector comprising a nucleic acid sequence encoding Akt3, the necessary elements for the transcription or translation of the nucleic acid; administering a test compound; and comparing the level of expression of the Akt3 with the level obtained with a control in the absence of the test compound.

The present invention provides detectably labeled oligonucleotides for imaging Akt3 polynucleotides within a cell. Such oligonucleotides are useful for determining if gene amplification has occurred, and for assaying the expression levels in a cell or tissue using, for example, in situ hybridization as is known in the art.

While the present invention has been described with specificity in accordance with certain of its preferred embodiments, the following examples serve only to illustrate the invention and are not intended to limit the invention.

EXAMPLES

Example 1

Antisense Inhibition of Target RNA

A. Preparation of Transfection Mixture

For each transfection mixture, a carrier molecule, preferably a lipitoid or cholesteroid, was prepared to a working concentration of 0.5 mM in water, sonicated to yield a uniform solution, and filtered through a 0.45 $\mu$m PVDF membrane. The antisense or control oligonucleotide (SEQ ID NO:1–27) was prepared to a working concentration of 100 $\mu$M in sterile Millipore water.

The oligonucleotide was diluted in OptiMEM™ (Gibco/BRL), in a microfuge tube, to 2 $\mu$M, or approximately 20 $\mu$g oligo/ml of OptiMEM™. In a separate microfuge tube, lipitoid or cholesteroid, typically in the amount of about 1.5–2 nmol lipitoid/$\mu$g antisense oligonucleotide, was diluted into the same volume of OptiMEM™ used to dilute the oligonucleotide. The diluted antisense oligonucleotide was immediately added to the diluted lipitoid and mixed by pipetting up and down.

B. Transfection

Cells were plated on tissue culture dishes one day in advance of transfection, in growth media with serum, to yield a density at transfection of 60–90%. The oligonucleotide/lipitoid mixture was added to the cells, immediately after mixing, to a final concentration of 100–300 nM antisense oligonucleotide. Cells were incubated with the transfection mixture at 37° C., 5% $CO_2$ for 4–24 hours. After incubation, the transfection mixture was removed and replaced with normal growth media with serum.

Total RNA was extracted using the RNeasy™ kit (Quiagen Corporation, Chatsworth, Calif.), according to manufacturer's protocols.

C. Reverse Transcription

The level of target mRNA was quantitated using the Roche LightCycler™ real-time PCR machine. Values for the target mRNA were normalized versus an internal control (e.g., beta-actin).

For each 20 ul reaction, extracted RNA (generally 0.2–1 µg total) was placed into a sterile 0.5 or 1.5 ml microcentrifuge tube, and water was added to a total volume of 12.5 µl. To each tube was added 7.5 µl of a buffer/enzyme mixture, prepared by mixing (in the order listed) 2.5 µl H$_2$O, 2.0 µl 10× reaction buffer, 10 µl oligo dT (20 pmol), 1.0 µl dNTP mix (10 mM each), 0.5 µl RNAsin® (20 u) (Ambion, Inc., Hialeah, Fla.), and 0.5 µl MMLV reverse transcriptase (50 u) (Ambion, Inc.). The contents were mixed by pipetting up and down, and the reaction mixture was incubated at 42° C. for 1 hour. The contents of each tube were centrifuged prior to amplification.

D. LightCycler™ Amplification of RT Reactions

An amplification mixture was prepared by mixing in the following order: 1× PCR buffer II, 3 mM MgCl$_2$, 140 µM each dNTP, 0.175 pmol each oligo, 1:50,000 dil of SYBR® Green, 0.25 mg/ml BSA, 1 unit Taq polymerase, and H$_2$O to 20 µl. (PCR buffer II is available in 10× concentration from Perkin-Elmer, Norwalk, Conn.). In 1× concentration it contains 10 mM Tris pH 8.3 and 50 mM KCl. SYBR® Green (Molecular Probes, Eugene, Oreg.) is a dye which fluoresces when bound to double stranded DNA. As double stranded PCR product is produced during amplification, the fluorescence from SYBR® Green increases.

To each 20 µl aliquot of amplification mixture, 2 µl of template RT was added, and amplification was carried out according to standard protocols.

As shown in FIG. 5 and in Table 1 below, Akt3 message levels were decreased relative to actin in SW620 cells.

TABLE 1

Effect of Akt3 Oligonucleotides on SW620 Proliferation

| Antisense oligonucleotide | Akt3 message levels normalized to actin |
| --- | --- |
| 18-1 AS SEQ ID NO:2 | 0.0000022 |
| 18-2 AS SEQ ID NO:3 | 0.0000018 |
| 18-3 AS SEQ ID NO:4 | 0.0000122 |
| 18-4 AS SEQ ID NO:5 | 0.0000025 |
| 18-5 AS SEQ ID NO:6 | 0.0000085 |
| 18-1 RC SEQ ID NO:7 | 0.000014 |
| 18-2 RC SEQ ID NO:8 | 0.0000075 |
| 18-3 RC SEQ ID NO:9 | 0.0000055 |

Cells were seeded into 96 well plates at a density of 5000 cells per well. For a 4 day proliferation assay, 5 independent 96 well plates were prepared, one for each day. After overnight incubation, cells were transfected using the procedure described above. On each day of the proliferation assay, all medium was removed from one plate and frozen at −70° C. On day four, all plates were developed with the Quantos™ assay kit (Stratagene, La Jolla, Calif.) which determines the amount of DNA, and thus the number of cells, in each well. The results are shown in FIGS. 1–3 and Tables 2–4 below.

TABLE 2

Effect of Akt3 Oligonucleotides on Growth of PC3 Cells

| Oligonucleotide | Day 0 | Day 1 | Day 2 | Day 3 | Day 4 |
| --- | --- | --- | --- | --- | --- |
| Wild type(no oligo) | 500 | 750 | 1100 | 1800 | 2400 |
| 18-1 AS | 500 | 500 | 480 | 480 | 500 |
| 18-1 RC | 500 | 550 | 700 | 800 | 800 |

TABLE 3

Effect of Akt3 Oligonucleotides on Growth of SKOV3 Cells

| Oligonucleotide | Day 0 | Day 1 | Day 2 | Day 3 | Day 4 |
| --- | --- | --- | --- | --- | --- |
| Wild type(no oligo) | 600 | 1200 | 1500 | 1800 | 3200 |
| 18-1 AS | 650 | 650 | 1100 | 700 | 900 |
| 18-1 RC | 700 | 1000 | 1350 | 2000 | 2700 |

TABLE 4

Effect of Akt3 Oligonucleotides on Growth of MDA231 Cells

| Oligonucleotide | Day 0 | Day 1 | Day 2 | Day 3 | Day 4 |
| --- | --- | --- | --- | --- | --- |
| Wild type (no oligo) | 600 | 1200 | 2200 | 2600 | 2600 |
| 18-1 AS | 600 | 700 | 1100 | 1400 | 1800 |
| 18-1 RC | 600 | 700 | 1250 | 1800 | 2300 |

P0703:   CGACAAATGGAAAAACAGCTCGCC (SEQ ID NO:2)

P1550:   TGGCTGGTCTGGGATGTCGGAAGG (SEQ ID NO:3)

P1674:   ACAGTAGCAGCAACAGCATGAGACC (SEQ ID NO:4)

P0197:   TTTGGCTTTGGTCGTTCGTTCTGTTTTCA (SEQ ID NO:5)

P0987:   CCCTAGGCCCCACCAGTCTACTGCT (SEQ ID NO:6)

P0703RC: CCGCTCGACAAAAAGGTAAACAGC (SEQ ID NO:7)

P1550RC: GGAAGGCGTAGGGTCTGGTCGGT (SEQ ID NO:8)

P1674RC: CCAGAGTACGACAACGACGATGACA (SEQ ID NO:9)

P0197RC: ACTTTTGTCTTGCTGGTTTCGGTTT (SEQ ID NO:10)

P0987RC: TCGTCATCTGACCACCCCGGATCCC (SEQ ID NO:11)

P687:    ACAGCTCGCCCCCATTAACATATTC (SEQ ID NO:12)

P714:    CACCCGCTCTCTCGACAATGGA (SEQ ID NO:13)

P720:    GAGAACACCCGCTCTCTCGCAAA (SEQ ID NO:14)

P737:    AACGTGTGCGGTCCTCAGAGACA (SEQ ID NO:15)

P768:    GTCCAAGGCAGAGCAATTTCTGCA (SEQ ID NO:16)

P812:    CTCCAACTTGGAATCACGGTACACA (SEQ ID NO:17)

P842:    TTATTGTGGCCATCTTTGTCCAGCAT (SEQ ID NO:18)

P890:    GCTCGATCTGTGATCCCTTCTTTGC (SEQ ID NO:19)

P687RC:  CTTATACAATACCCCCGCTCGACA (SEQ ID NO:20)

-continued

P714RC: AAAGGTAACAGCTCTCTCGCCCAC (SEQ ID NO:21)

P720RC: AAACAGCTCTCTCGCCCACAAGAG (SEQ ID NO:22)

P737RC: ACAAGAGACTCCTGGCGTGTGCAA (SEQ ID NO:23)

P768RC: ACGTGTTTAACAGAGACGGAACCTG (SEQ ID NO:24)

P812RC: ACACATGGCACTAGAGTTCAACCTC (SEQ ID NO:25)

P842RC: TACGACCTGTTTCTACCGGTGTATT (SEQ ID NO:26)

P890RC: CGTTTCTTCCCTAGTGTCTACGTCG (SEQ ID NO:27)

From the foregoing it will be appreciated that, although specific embodiments of the invention have been described herein for purposes of illustration, various modifications may be made without departing from the spirit and scope of the invention. Accordingly, the invention is not limited except as by the appended claims.

What is claimed is:

1. An isolated Akt3 inhibitor wherein said inhibitor is an antisense molecule, and wherein said antisense molecule comprises a nucleic acid sequence selected from the group consisting of SEQ ID NOS:2, 3, 4, 5, 6, 12, 13, 14, 15, 16, 17, 18 and 19, wherein said antisense molecule is not longer than 35 nucleotides in length and is capable of inhibiting the expression of human Akt3.

2. A composition comprising a therapeutically effective amount of an Akt3 antisense molecule, wherein said antisense molecule comprises a nucleic acid sequence selected from the group consisting of SEQ ID NOS: 2, 3, 4, 5, 6, 12, 13, 14, 15, 16, 17, 18 and 19.

3. A method of decreasing the expression of Akt3 in a mammalian cell in vitro, comprising administering to said cell an Akt3 inhibitor wherein said Akt3 inhibitor is an antisense molecule selected from the group consisting of SEQ ID NOS: 2, 3, 4, 5, 6, 12, 13, 14, 15, 16, 17, 18 and 19.

4. An isolated polynucleotide comprising:
  a. a polynucleotide comprising a transcription initiation region; and
  b. a polynucleotide sequence encoding an antisense oligonucleotide at least 8 nucleotides or nucleotide analogues and not longer than 35 nucleotides in length comprising a sequence selected from the group consisting of SEQ ID NOS:2, 3, 4, 5, 6, 12, 13, 14, 15, 16, 17, 18 and 19.

5. A recombinant vector comprising the isolated polynucleotide of claim 4.

* * * * *

SEQUENCE LISTING

<160> NUMBER OF SEQ ID NOS: 27

<210> SEQ ID NO 1
<211> LENGTH: 1547
<212> TYPE: DNA
<213> ORGANISM: Homo sapiens

<400> SEQUENCE: 1

```
gggagtcatc atgagcgatg ttaccattgt gaaagaaggt tgggttcaga agaggggaga      60
atatataaaa aactggaggc caagatactt ccttttgaag acagatggct cattcatagg     120
atataaagag aaacctcaag atgtggattt accttatccc ctcaacaact tttcagtggc     180
aaaatgccag ttaatgaaaa cagaacgacc aaagccaaac acatttataa tcagatgtct     240
ccagtggact actgttatag agagaacatt tcatgtagat actccagagg aaagggaaga     300
atggacagaa gctatccagg ctgtagcaga cagactgcag aggcaagaag aggagagaat     360
gaattgtagt ccaacttcac aaattgataa tataggagag gaagagatgg atgcctctac     420
aacccatcat aaaagaaaga caatgaatga ttttgactat ttgaaactac taggtaaagg     480
cacttttggg aaagttattt tggttcgaga gaaggcaagt ggaaaatact atgctatgaa     540
gattctgaag aaagaagtca ttattgcaaa ggatgaagtg gcacacactc taactgaaag     600
cagagtatta aagaacacta gacatccctt tttaacatcc ttgaaatatt ccttccagac     660
aaaagaccgt ttgtgttttg tgatggaata tgttaatggg ggcgagctgt ttttccattt     720
gtcgagagag cgggtgttct ctgaggaccg cacacgtttc tatggtgcag aaattgtctc     780
tgccttggac tatctacatt ccggaaagat tgtgtaccgt gatctcaagt tggagaatct     840
aatgctggac aaagatggcc acataaaaat tacagatttt ggactttgca agaagggat     900
cacagatgca gccaccatga agacattctg tggcactcca gaatatctgg caccagaggt     960
gttagaagat aatgactatg gccgagcagt agactggtgg ggcctagggg ttgtcatgta    1020
tgaaatgatg tgtgggaggt taccttttcta caaccaggac catgagaaac ttttttgaatt    1080
aatattaatg gaagacatta aattttcctcg aacactctct tcagatgcaa aatcattgct    1140
ttcagggctc ttgataaagg atccaaataa acgccttggt ggaggaccag atgatgcaaa    1200
agaaattatg agacacagtt tcttctctgg agtaaactgg caagatgtat atgataaaaa    1260
gcttgtacct ccttttaaac ctcaagtaac atctgagaca gatactagat attttgatga    1320
agaatttaca gctcagacta ttacaataac accacctgaa aaatatgatg aggatggtat    1380
ggactgcatg gacaatgaga ggcggccgca tttccctcaa ttttcctact ctgcaagtgg    1440
acgagaataa gtctcttttca ttctgctact tcactgtcat cttcaattta ttactgaaaa    1500
```

```
tgattcctgg acatcaccag tcctagctct tacacatagc aggggca            1547

<210> SEQ ID NO 2
<211> LENGTH: 24
<212> TYPE: DNA
<213> ORGANISM: Artificial Sequence
<220> FEATURE:
<223> OTHER INFORMATION: oligonucleotide

<400> SEQUENCE: 2
cgacaaatgg aaaaacagct cgcc                                      24

<210> SEQ ID NO 3
<211> LENGTH: 24
<212> TYPE: DNA
<213> ORGANISM: Artificial Sequence
<220> FEATURE:
<223> OTHER INFORMATION: oligonucleotide

<400> SEQUENCE: 3
tggctggtct gggatgtcgg aagg                                      24

<210> SEQ ID NO 4
<211> LENGTH: 25
<212> TYPE: DNA
<213> ORGANISM: Artificial Sequence
<220> FEATURE:
<223> OTHER INFORMATION: oligonucleotide

<400> SEQUENCE: 4
acagtagcag caacagcatg agacc                                     25

<210> SEQ ID NO 5
<211> LENGTH: 29
<212> TYPE: DNA
<213> ORGANISM: Artificial Sequence
<220> FEATURE:
<223> OTHER INFORMATION: oligonucleotide

<400> SEQUENCE: 5
tttggctttg gtcgttcgtt ctgttttca                                 29

<210> SEQ ID NO 6
<211> LENGTH: 25
<212> TYPE: DNA
<213> ORGANISM: Artificial Sequence
<220> FEATURE:
<223> OTHER INFORMATION: oligonucleotide

<400> SEQUENCE: 6
ccctaggccc caccagtcta ctgct                                     25

<210> SEQ ID NO 7
<211> LENGTH: 24
<212> TYPE: DNA
<213> ORGANISM: Artificial Sequence
<220> FEATURE:
<223> OTHER INFORMATION: oligonucleotide

<400> SEQUENCE: 7
ccgctcgaca aaaggtaaa cagc                                       24

<210> SEQ ID NO 8
<211> LENGTH: 23
<212> TYPE: DNA
```

```
<213> ORGANISM: Artificial Sequence
<220> FEATURE:
<223> OTHER INFORMATION: oligonucleotide

<400> SEQUENCE: 8
ggaaggcgta gggtctggtc ggt                                        23

<210> SEQ ID NO 9
<211> LENGTH: 25
<212> TYPE: DNA
<213> ORGANISM: Artificial Sequence
<220> FEATURE:
<223> OTHER INFORMATION: oligonucleotide

<400> SEQUENCE: 9
ccagagtacg acaacgacga tgaca                                      25

<210> SEQ ID NO 10
<211> LENGTH: 25
<212> TYPE: DNA
<213> ORGANISM: Artificial Sequence
<220> FEATURE:
<223> OTHER INFORMATION: oligonucleotide

<400> SEQUENCE: 10
acttttgtct tgctggtttc ggttt                                      25

<210> SEQ ID NO 11
<211> LENGTH: 25
<212> TYPE: DNA
<213> ORGANISM: Artificial Sequence
<220> FEATURE:
<223> OTHER INFORMATION: oligonucleotide

<400> SEQUENCE: 11
tcgtcatctg accaccccgg atccc                                      25

<210> SEQ ID NO 12
<211> LENGTH: 25
<212> TYPE: DNA
<213> ORGANISM: Artificial Sequence
<220> FEATURE:
<223> OTHER INFORMATION: oligonucleotide

<400> SEQUENCE: 12
acagctcgcc cccattaaca tattc                                      25

<210> SEQ ID NO 13
<211> LENGTH: 22
<212> TYPE: DNA
<213> ORGANISM: Artificial Sequence
<220> FEATURE:
<223> OTHER INFORMATION: oligonucleotide

<400> SEQUENCE: 13
cacccgctct ctcgacaatg ga                                         22

<210> SEQ ID NO 14
<211> LENGTH: 23
<212> TYPE: DNA
<213> ORGANISM: Artificial Sequence
<220> FEATURE:
<223> OTHER INFORMATION: oligonucleotide

<400> SEQUENCE: 14
gagaacaccc gctctctcgc aaa                                        23
```

<210> SEQ ID NO 15
<211> LENGTH: 23
<212> TYPE: DNA
<213> ORGANISM: Artificial Sequence
<220> FEATURE:
<223> OTHER INFORMATION: oligonucleotide

<400> SEQUENCE: 15
aacgtgtgcg gtcctcagag aca                                           23

<210> SEQ ID NO 16
<211> LENGTH: 24
<212> TYPE: DNA
<213> ORGANISM: Artificial Sequence
<220> FEATURE:
<223> OTHER INFORMATION: oligonucleotide

<400> SEQUENCE: 16
gtccaaggca gagcaatttc tgca                                          24

<210> SEQ ID NO 17
<211> LENGTH: 25
<212> TYPE: DNA
<213> ORGANISM: Artificial Sequence
<220> FEATURE:
<223> OTHER INFORMATION: oligonucleotide

<400> SEQUENCE: 17
ctccaacttg gaatcacggt acaca                                         25

<210> SEQ ID NO 18
<211> LENGTH: 26
<212> TYPE: DNA
<213> ORGANISM: Artificial Sequence
<220> FEATURE:
<223> OTHER INFORMATION: oligonucleotide

<400> SEQUENCE: 18
ttattgtggc catctttgtc cagcat                                        26

<210> SEQ ID NO 19
<211> LENGTH: 25
<212> TYPE: DNA
<213> ORGANISM: Artificial Sequence
<220> FEATURE:
<223> OTHER INFORMATION: oligonucleotide

<400> SEQUENCE: 19
gctcgatctg tgatcccttc tttgc                                         25

<210> SEQ ID NO 20
<211> LENGTH: 24
<212> TYPE: DNA
<213> ORGANISM: Artificial Sequence
<220> FEATURE:
<223> OTHER INFORMATION: oligonucleotide

<400> SEQUENCE: 20
cttatacaat accccgctc gaca                                           24

<210> SEQ ID NO 21
<211> LENGTH: 24
<212> TYPE: DNA
<213> ORGANISM: Artificial Sequence
<220> FEATURE:

```
<223> OTHER INFORMATION: oligonucleotide

<400> SEQUENCE: 21
aaaggtaaca gctctctcgc ccac                                              24

<210> SEQ ID NO 22
<211> LENGTH: 24
<212> TYPE: DNA
<213> ORGANISM: Artificial Sequence
<220> FEATURE:
<223> OTHER INFORMATION: oligonucleotide

<400> SEQUENCE: 22
aaacagctct ctcgcccaca agag                                              24

<210> SEQ ID NO 23
<211> LENGTH: 24
<212> TYPE: DNA
<213> ORGANISM: Artificial Sequence
<220> FEATURE:
<223> OTHER INFORMATION: oligonucleotide

<400> SEQUENCE: 23
acaagagact cctggcgtgt gcaa                                              24

<210> SEQ ID NO 24
<211> LENGTH: 25
<212> TYPE: DNA
<213> ORGANISM: Artificial Sequence
<220> FEATURE:
<223> OTHER INFORMATION: oligonucleotide

<400> SEQUENCE: 24
acgtgtttaa cagagacgga acctg                                             25

<210> SEQ ID NO 25
<211> LENGTH: 25
<212> TYPE: DNA
<213> ORGANISM: Artificial Sequence
<220> FEATURE:
<223> OTHER INFORMATION: oligonucleotide

<400> SEQUENCE: 25
acacatggca ctagagttca acctc                                             25

<210> SEQ ID NO 26
<211> LENGTH: 25
<212> TYPE: DNA
<213> ORGANISM: Artificial Sequence
<220> FEATURE:
<223> OTHER INFORMATION: oligonucleotide

<400> SEQUENCE: 26
tacgacctgt ttctaccggt gtatt                                             25

<210> SEQ ID NO 27
<211> LENGTH: 25
<212> TYPE: DNA
<213> ORGANISM: Artificial Sequence
<220> FEATURE:
<223> OTHER INFORMATION: oligonucleotide

<400> SEQUENCE: 27
cgtttcttcc ctagtgtcta cgtcg                                             25
```